(12) United States Patent
Dennis

(10) Patent No.: US 6,730,097 B2
(45) Date of Patent: May 4, 2004

(54) SURGICAL SNARE WITH STEERING TETHER AND METHOD OF USING SAME

(76) Inventor: William G. Dennis, c/o 11222-4 St. Johns Industrial Pkwy., Jacksonville, FL (US) 32246

( * ) Notice: Subject to any disclaimer, the term of this patent is extended or adjusted under 35 U.S.C. 154(b) by 43 days.

(21) Appl. No.: 10/006,042

(22) Filed: Dec. 7, 2001

(65) Prior Publication Data
US 2003/0109874 A1 Jun. 12, 2003

(51) Int. Cl.[7] .............................................. A61B 17/32
(52) U.S. Cl. ........................ 606/113; 606/110; 606/47
(58) Field of Search .............................. 606/45, 46, 47, 606/110, 111, 113, 114

(56) References Cited

U.S. PATENT DOCUMENTS

| | | | |
|---|---|---|---|
| 3,791,387 A | * 2/1974 | Itoh | 128/320 |
| 4,950,273 A | 8/1990 | Briggs | |
| 5,304,183 A | 4/1994 | Gourlay et al. | |
| 5,730,704 A | * 3/1998 | Avitall | 600/374 |
| 5,738,683 A | * 4/1998 | Osypka | 606/47 |
| 5,759,187 A | * 6/1998 | Nakao et al. | 606/114 |
| 5,800,444 A | 9/1998 | Ridinger et al. | |
| 5,814,052 A | 9/1998 | Nakao et al. | |
| 5,823,956 A | * 10/1998 | Roth et al. | 600/374 |
| 5,906,620 A | 5/1999 | Nakao et al. | |
| 6,071,281 A | * 6/2000 | Burnside et al. | 606/41 |
| 6,258,101 B1 | 7/2001 | Blake, III | |

* cited by examiner

Primary Examiner—Michael Peffley
Assistant Examiner—Aaron Roane
(74) Attorney, Agent, or Firm—Hunton & Williams

(57) ABSTRACT

A surgical instrument and method for facilitating the capture of objects during surgery are provided. The surgical instrument comprises a flexible tube having a proximal tube end and a distal tube end, the flexible tube defining a cable passageway and being configured for insertion of at least a distal portion of the flexible tube into a body cavity of a patient. The surgical instrument further comprises a flexible cable having a proximal cable end and a distal cable end. At least a portion of the flexible cable is slidably disposed in the cable passageway. A snare loop having a loop member is attached to the distal cable end. The snare loop and the cable are adapted so that the snare loop can be selectively retracted within the cable passageway by sliding the flexible cable proximally within the cable passageway. The snare loop and the cable are also adapted so that at least a portion of the snare loop can be selectively extended from the distal tube end by sliding the flexible cable distally within the cable passageway. The loop member is adapted for selectively encircling and engaging at least a portion of an object in the body cavity. The system also comprises a steering tether having a proximal tether end and a distal tether end. The distal tether end is attached to the loop member so that application of a tensile force to the proximal tether end causes the snare loop to deform in a predetermined manner, thereby facilitating a maneuvering of the snare loop.

26 Claims, 18 Drawing Sheets

SURGICAL SNARE WITH STEERING TETHER AND METHOD OF USING SAME

BACKGROUND OF THE INVENTION

This invention relates generally to surgical instruments and more particularly to instruments such as snares that may be used for grasping and removing material during surgery.

During surgery, there is often a need for the collection and removal of tissue specimens such as polyps or other material from a body cavity of the patient. The removal of such tissue is often accomplished through the use of a snare device or slip-knotted suture loop that is inserted into the patient through a cannula. The snare device is generally mounted to the end of a cable slidably disposed within a flexible tube. The user of the snare device must maneuver the end of the flexible tube and cable through the body cavity, which may have a number of convolutions such as in the case of an intestinal cavity. The snare must then be maneuvered so as to surround the material to be grasped and then cinched around the material, typically using an external actuation mechanism.

The maneuverability of the snare device is generally limited to motion resulting from extension or retraction of the snare from the end of the flexible tube, extension or retraction of the flexible tube and the cable/rod and, under certain circumstances, rotation of the flexible tube and the cable/rod. This limited maneuverability can make it difficult to position the snare around the material of interest, particularly in areas where there is little room for repositioning of the tube and/or cannula.

SUMMARY OF THE INVENTION

There is accordingly a need for a surgical instrument snare with an additional manipulation capability that facilitates the maneuvering of the snare to encircle material within a body cavity of a patient.

Accordingly, an embodiment of the present invention provides a surgical instrument for facilitating the capture of objects during surgery. The surgical instrument comprises a flexible tube having a proximal tube end and a distal tube end, the flexible tube defining a cable passageway and being configured for insertion of at least a distal portion of the flexible tube into a body cavity of a patient. The surgical instrument further comprises a flexible cable having a proximal cable end and a distal cable end. At least a portion of the flexible cable is slidably disposed in the cable passageway. A snare loop having a loop member is attached to the distal cable end. The snare loop and the cable are adapted so that the snare loop can be selectively retracted within the cable passageway by sliding the flexible cable proximally within the cable passageway. The snare loop and the cable are also adapted so that at least a portion of the snare loop can be selectively extended from the distal tube end by sliding the flexible cable distally within the cable passageway. The loop member is adapted for selectively encircling and engaging at least a portion of an object in the body cavity. The system also comprises a steering tether having a proximal tether end and a distal tether end. The distal tether end is attached to the loop member so that application of a tensile force to the proximal tether end causes the snare loop to deform in a predetermined manner, thereby facilitating a maneuvering of the snare loop.

Another aspect of the invention provides a surgical instrument for facilitating the capture of objects during surgery. The surgical instrument comprises a snare control module having a body with a distal body end and a proximal body end. The snare control module also has a control slide with a passage formed therein for slidable disposition of at least a portion of the body therethrough. The surgical instrument further comprises a flexible tube having a proximal tube end attached to the distal end of the body and a distal tube end. The flexible tube defines a cable passageway and is configured for insertion of at least a distal portion of the flexible tube into a body cavity of a patient. The surgical instrument still further comprises a flexible cable having a proximal cable end and a distal cable end. At least a portion of the flexible cable is slidably disposed in the cable passageway. The proximal cable end is connected to the control slide so that movement of the control slide toward the proximal body end causes proximal movement of the flexible cable within the cable passageway and movement of the control slide toward the distal body end causes distal movement of the flexible cable within the cable passageway. The instrument also comprises a snare loop having a loop member attached to the distal cable end. The snare loop and the cable are adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway. The loop member is adapted for selectively encircling and engaging at least a portion of an object in the body cavity. The surgical instrument further comprises at least one steering tether having a proximal tether end and a distal tether end. The distal tether end of each of the at least one steering tether is attached to the loop member so that application of a tensile force to the proximal tether end causes the snare loop to deform in a predetermined manner, thereby facilitating a maneuvering of the snare loop.

Yet another aspect of the invention provides a method of securing an object disposed within a body cavity of a patient using a surgical instrument of the invention. The surgical instrument has a flexible tube having distal and proximal tube ends and defining a cable passageway, a flexible cable having proximal and distal cable ends and being slidably disposed in the cable passageway, a snare loop attached to the distal cable end, the snare loop and the cable being adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway, and a steering tether having a proximal tether end and a distal tether end, the distal tether end being attached to the snare loop. The method comprises inserting the distal end of the flexible tube and the snare loop into the body cavity through a cannula while retaining the proximal tether end outside the body cavity. The method further comprises maneuvering the distal end of the flexible tube through the body cavity until the snare loop is positioned adjacent the object. The method still further comprises placing the steering tether in tension by pulling on the proximal tether end and applying a tensile force to the steering tether sufficient to cause the snare loop to deform in an efficacious manner to facilitate positioning of the snare loop around at least a portion of the object. The method still further comprises maneuvering the snare loop to encircle at least a portion of the object.

Other objects and advantages of the invention will be apparent to one of ordinary skill in the art upon reviewing the detailed description of the invention.

DETAILED DESCRIPTION OF THE INVENTION

The present invention provides a surgical instrument that includes a steering tether that allows a surgeon to remotely manipulate a snare loop to maneuver the snare loop in position around an object or tissue inside a body cavity of a patient.

Figure 1:
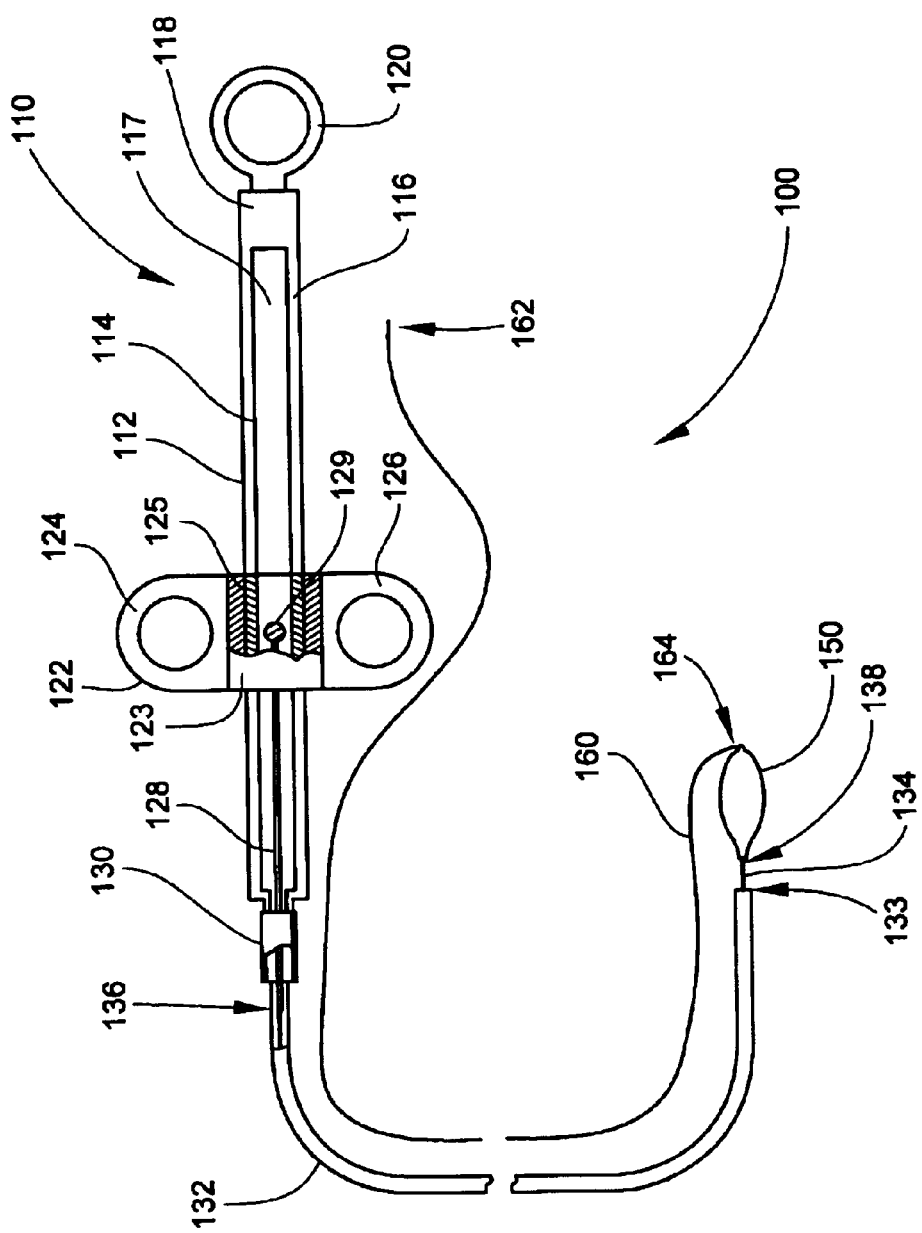
FIG. 1 is a partially sectioned view of a surgical instrument according to an embodiment of the invention.
Figure 2:
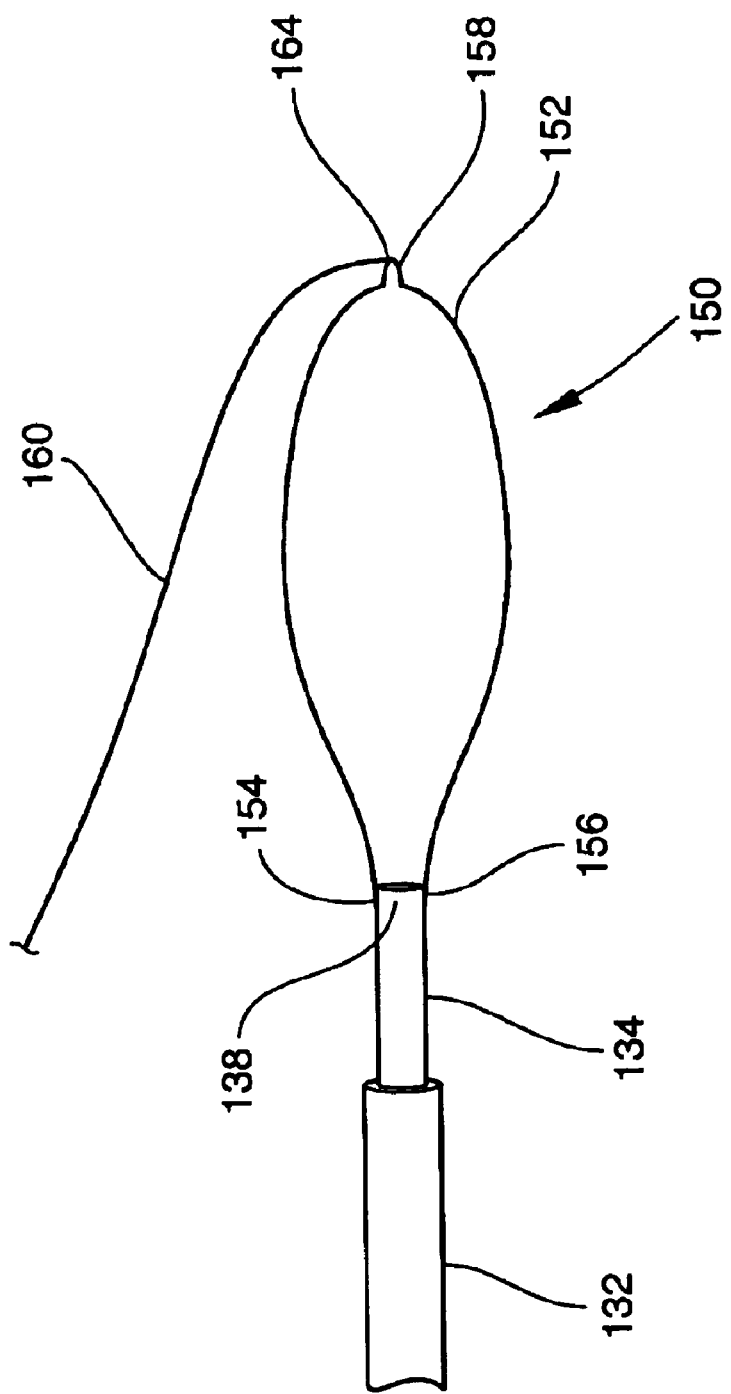
FIG. 2 is a perspective view of a snare loop of the surgical instrument illustrated in FIG. 1.

FIGS. 1 and 2 illustrate a surgical instrument 100 according to an embodiment of the invention. The surgical instrument 100 includes a snare control module 110 that is used to control the deployment and retraction of a snare loop 150 from a flexible tube 132. The snare loop 150 is formed from a resilient loop member 152. The loop member 152 has first and second ends 154, 156 that are attached to a flexible cable 134 at its distal end 138. The resilient loop member 152 may take the form of a wire, cable or band formed from metal or a resilient surgical plastic. The resilient loop member 152 may also be a suture material attached to a biasing member or material. The resilient loop member 152 may be formed from an electrically conductive material for use as a cauterization loop. The loop member 152 may be attached to the cable 134 in any conventional manner such as bonding or welding.

The flexible cable 134 is slidably disposed within a flexible tube 132 formed from a polymer or other material suitable for use in surgical applications. The flexible tube 132 has an inside diameter sized to accommodate the cable 134 and the snare loop 150. In particular, the tube 132 is sized so that the snare loop 150 can be easily retracted into the distal end 133 of the tube 132 when the cable 134 is moved proximally relative to the tube 132 and extended out of and from the tube 132 when the cable is moved distally relative to the tube 132.

The snare loop 150 is formed so that when freed from the flexible tube 132, it will form a substantially elliptical loop that can be used to encircle an object. As the ends 154, 156 of the resilient loop member 152 are drawn into the flexible tube 132, the loop member 152 is cinched to a smaller and smaller loop. If an object is encircled by the loop member 152, the loop member 152 can be tightened around the object to secure the snare loop 150 to the object. If no object is encircled, the snare loop 150 may be drawn within the flexible tube 132.

The loop member 152 may be formed so as to include an extension 158 that extends outward from the distal end of the elliptical loop formed by the loop member 152. Such an extension can be used to facilitate the capture and retrieval of certain objects.

The snare control module 110 may be used to control the retraction and extension of the snare loop 150 from the tube 132. The snare control module 110 has a generally cylindrical body 112, a control slide 122, an actuation rod 128 and a tube connector 130. The body 112 of the snare control module 110 is formed by two frame members 114, 116 and a proximal end portion 118. The frame members 114, 116 and the end portion 118 may be integrally formed into a single body structure. The frame members 114, 116 define a central frame opening 117 that runs diametrically through the body 112.

The control slide 122 has a central portion 123 having a cylindrical passage 125 formed therethrough. The cylindrical passage 125 is sized to slidably accommodate the body 112 within the cylindrical passage 125. This allows the control slide 122 to be reciprocated along the body 112.

The proximal end 135 of the flexible tube 132 is attached to the distal end of the body by a hollow, cylindrical connector 130. Alternatively, the tube 132 may have a flange (not shown) at its proximal end 135 that can be used to hold the proximal end 135 in place within the connector 130. The connector 130 may be attached to the body 112 by internal threads configured to mate with external threads on the frame members 114, 116.

An actuation rod 128 is attached at one end to the proximal end 136 of the cable 134 and at its other end to an actuation rod pin 129 attached to the central portion 123 of the control slide 122. The actuation rod pin 129 is positioned diametrically across the cylindrical passage 125 within the central frame opening 117 so that it does not impede the reciprocal motion of the control slide 122. When the control slide 122 is moved toward the proximal end of the body 112, the actuation rod 128 also moves in this direction, which, in turn, moves the proximal end 136 of the cable 134 proximally relative to the flexible tube 132. When the control slide 122 is moved away from the proximal end of the body 112, the actuation rod 128 moves the proximal end 136 of the cable 134 distally relative to the flexible tube 132.

The reciprocal motion of the control slide 122 can thus be used to control the deployment of the snare loop 150 from and the retraction of the snare loop into the distal end 133 of the flexible tube 132. Moving the control slide 122 distally causes the snare loop 150 to be extended from the flexible tube 132. Moving the control slide 122 proximally causes the withdrawal of the snare loop 150 toward and into the flexible tube 132.

To facilitate one hand control of the reciprocal motion of the control slide 122, finger rings 124, 126 may be attached to the central portion 123 of the control slide 122 and a thumb ring 120 may be attached to the proximal portion 118 of the body 112.

It will be understood by those having ordinary skill in the art that other mechanisms could be used in the snare control module 110 without departing from the scope and spirit of the present invention. Such mechanisms may include, for example, slide actuators without finger rings and actuators configured for use in electro-cautery.

The surgical instrument 100 also includes a steering tether 160 that can be used to assist in maneuvering the snare loop 150. The steering tether 160 has a distal end 164 that is attached to the loop member 152 and a proximal end 162 that is passed out of the patient's body. The distal end 164 of the steering tether 160 may be attached to the loop member 152 anywhere around the circumference of the loop formed by the loop member 152. In the embodiment illustrated in FIGS. 1 and 2, the distal end 164 of the steering tether 160 is attached at the distal-most point on the loop member 152. As will be discussed, hereinafter, this positioning of the tether attachment is particularly useful in assisting the surgeon in maneuvering the snare loop 150 over an object such as a polyp.

The steering tether 160 may be formed from any thread-like structure including but not limited to thread, wire, cable and chain. The steering tether 160 may be formed from any suitable material including but not limited to steel or other metal, polymeric materials such as nylon, and twisted cotton or other textile materials.

The proximal end 162 of the steering tether 160 may be placed and/or attached to any arrangement that facilitates the grasping of the steering tether 160 at or near the proximal end 162 to apply tension to the tether 162. For example, the proximal end 162 may be attached to a ring or other type of handle, tied to a structure external to the patient, or attached to the snare control module 110 in any conventional manner. The proximal end 162 may also be left as a free end for a surgeon to tie off when and if desired.

Figure 3:
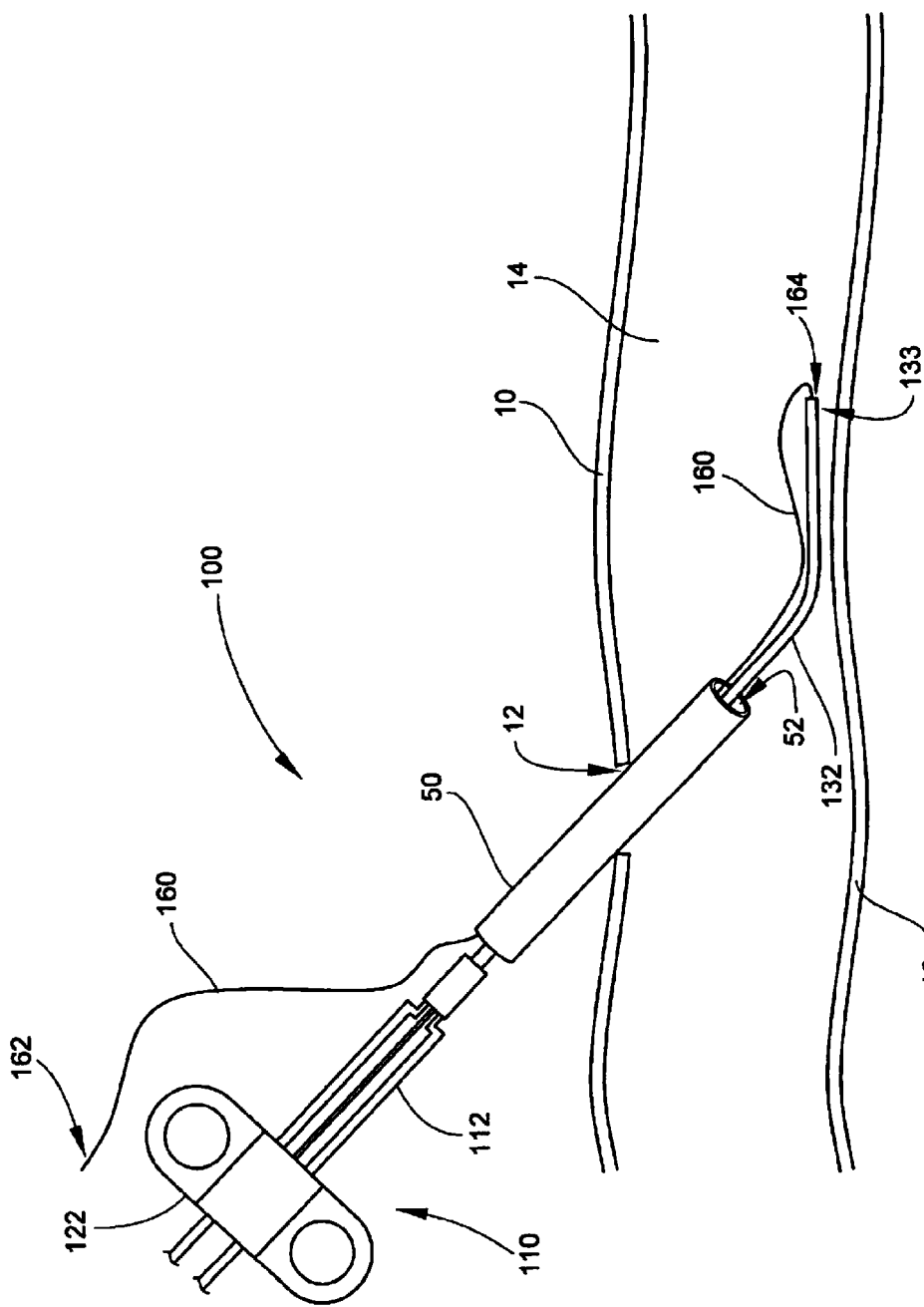
FIG. 3 is a view of the surgical instrument of FIG. 1 partially inserted into a body cavity through a cannula.
Figure 4:
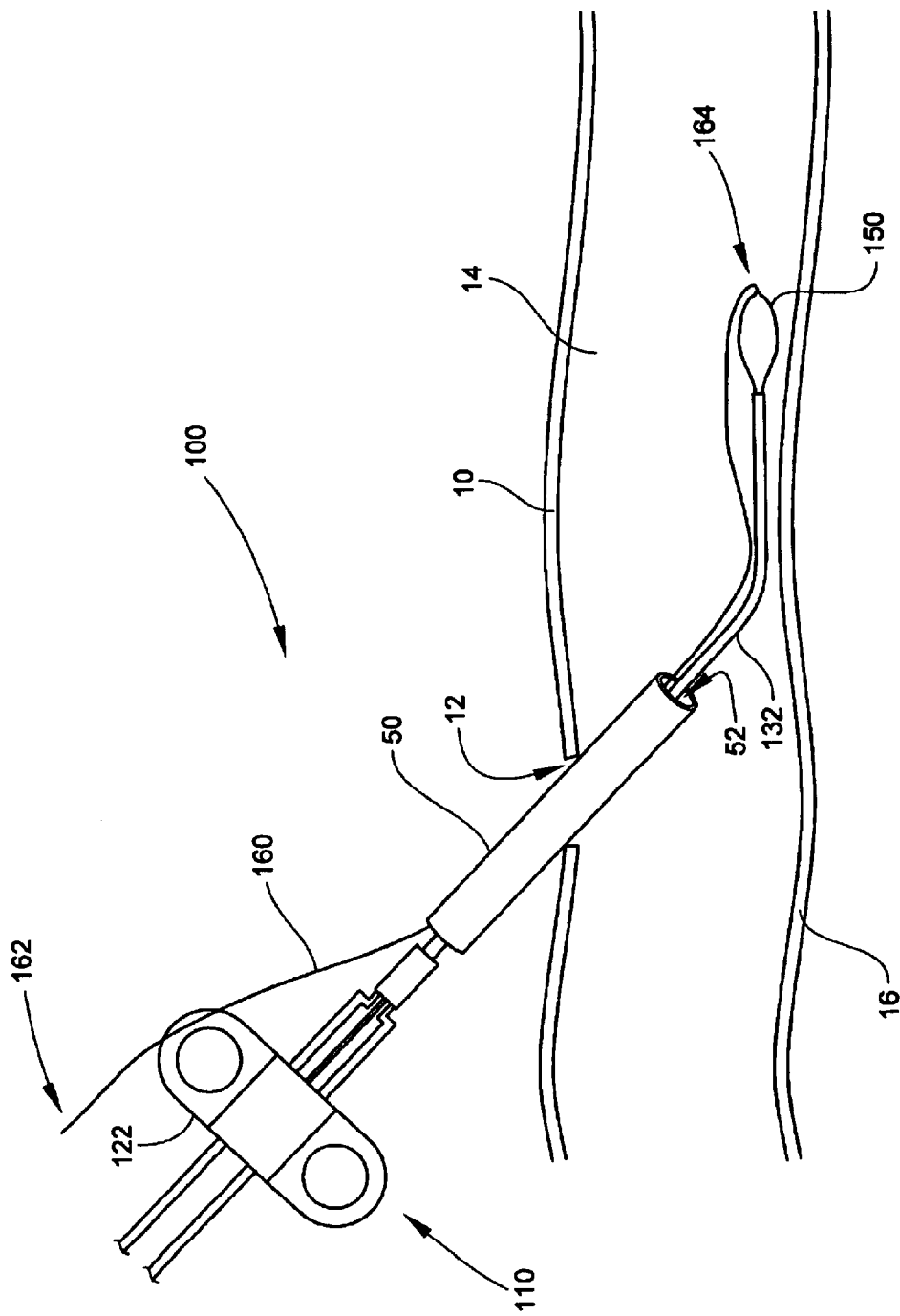
FIG. 4 is a view of the surgical instrument of FIG. 3 with its snare loop deployed.

Turning now to FIGS. 3 and 4, the flexible tube 132 and the snare loop 150 may be introduced into a body cavity 14 through the lumen 52 of a cannula 50. The body cavity 14 is defined by first and second tissue walls 10 and 16. The cannula 50 has been inserted through an opening 12 in the first tissue layer 10. The distal end 133 of the flexible tube 132 may be passed through the cannula 50 into the cavity 14 with the snare loop 150 retracted within the tube 132 as shown in FIG. 3. In this configuration, the distal end 164 of the steering tether 160, which is attached to the snare loop 150 is also withdrawn within the tube 132. When the tube 132 is inserted through the lumen 52, the proximal end 162 of the steering tether 160 is held so that the distal portion of the steering tether 160 is passed through the lumen 52 along with the tube 132. The proximal end 160 remains outside of the body cavity 14 and the cannula 50.

Under certain circumstances, it may be advantageous or necessary to allow the full length of the steering tether 160 to be inserted into the cavity 14. This leaves the proximal end 162 of the steering tether 160 inside the body cavity 14 where it can be later grasped to apply tension to the steering tether 160.

The tube 132 and the cable 134 are formed so as to be sufficiently flexible to pass through any curves in the cavity 14 that may be encountered as the tube 132 is inserted. Once the tube 132 has been inserted and positioned near the area of interest, the control slide 122 of the snare control module 110 can be moved in the distal direction relative to the body 112 to cause the snare loop 150 to be extended as shown in FIG. 4. It will be understood that, depending on the relative sizes of the snare loop 150 and the cannula lumen 52, it may be possible to insert the tube 132 through the cannula 50 with the snare loop 150 already deployed. In either case, the snare loop 150 and the steering tether 160 may be positioned within the cavity 14 as shown in FIG. 4.

Figure 5:
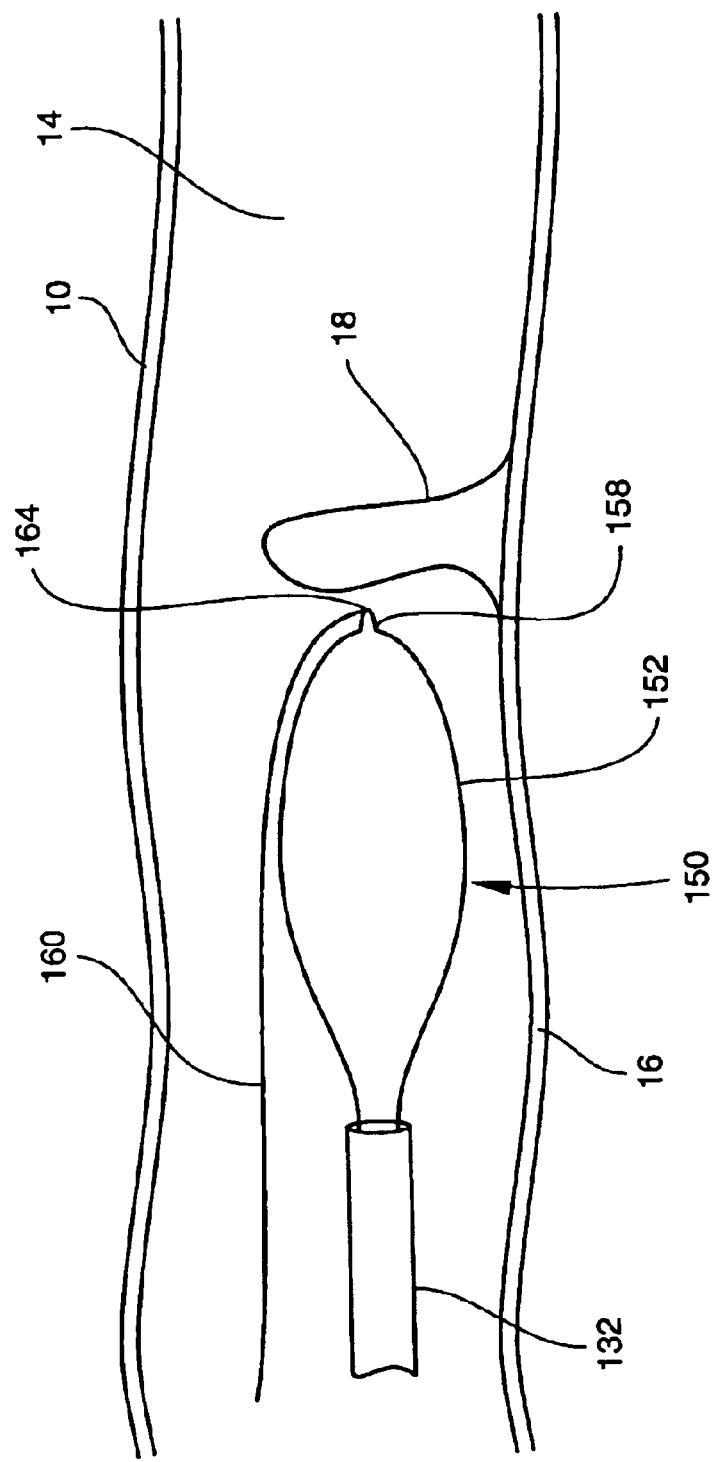
FIG. 5 is a perspective view of a snare loop of a surgical instrument according to the invention illustrating a step in a sequence of encircling a polyp with the snare loop.
Figure 6:
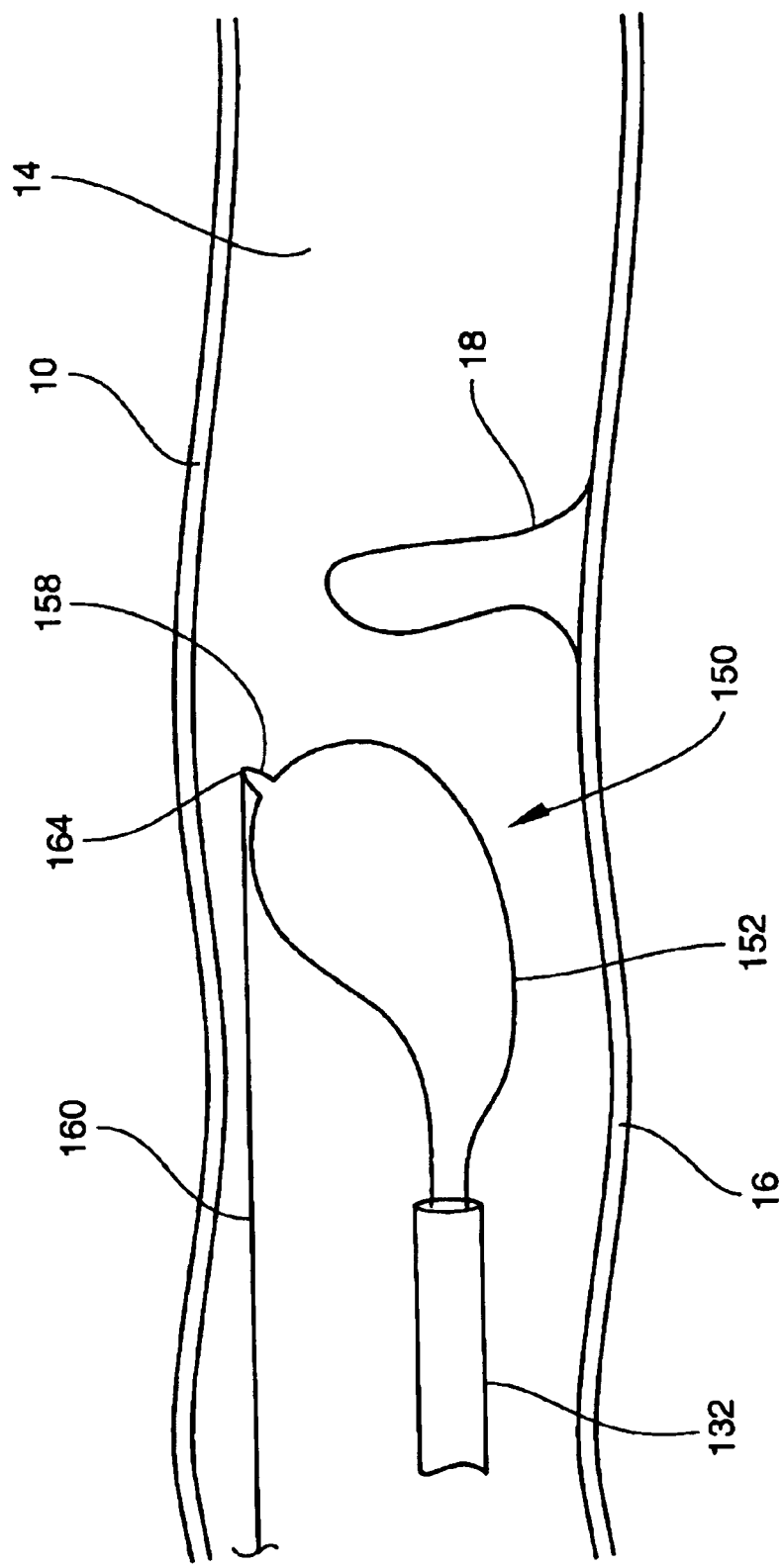
FIG. 6 is a perspective view of a snare loop of a surgical instrument according to the invention illustrating another step in a sequence of encircling a polyp with the snare loop.
Figure 7:
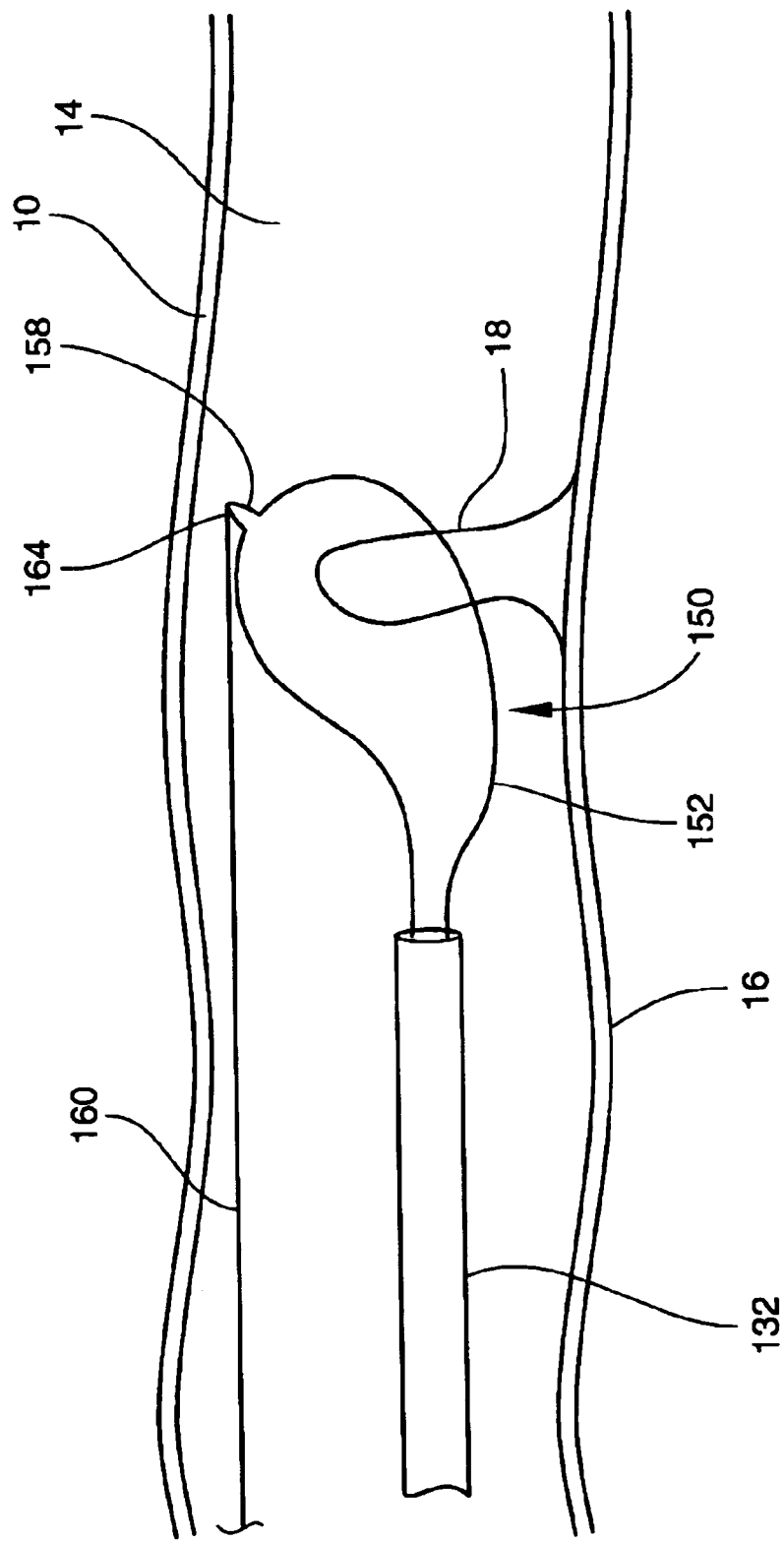
FIG. 7 is a perspective view of a snare loop of a surgical instrument according to the invention illustrating another step in a sequence of encircling a polyp with the snare loop.
Figure 8:
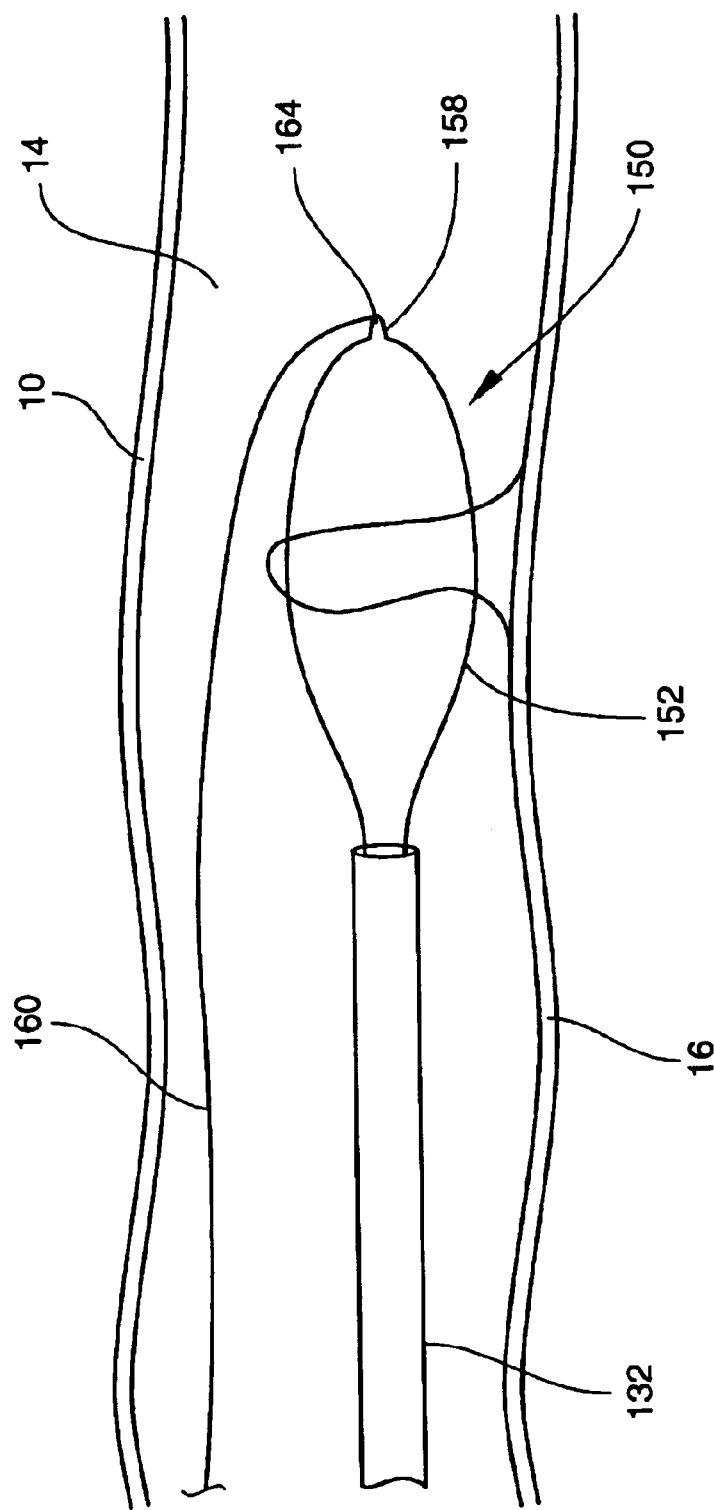
FIG. 8 is a perspective view of a snare loop of a surgical instrument according to the invention illustrating another step in a sequence of encircling a polyp with the snare loop.

FIGS. 5–8 illustrate a sequence by which the snare loop 150 can be used to encircle a polyp 18 attached to the lower tissue wall 16. As initially deployed from the tube 132, the steering tether 160 is relatively slack and the snare loop 150 is at a level where it cannot be positioned over the top of the polyp 18 (FIG. 5). This problem can occur as a result of the geometry of the cavity 14 and the stiffness of the tube 132. The steering tether 160, however, provides a way of deforming the snare loop 150 to overcome the problem. By pulling on the proximal end 162 of the steering tether 160, a surgeon can place the steering tether 160 in tension. As shown in FIG. 6, the tensile force transmitted through the steering tether 160 causes the snare loop 150 to be deformed so that the distal portion of the snare loop member 152 may be raised above the level of the polyp as shown in FIG. 6. With the snare loop 150 raised, the tube 132 can then be translated further into the cavity 14 to position the snare loop 150 over the polyp 18 as shown in FIG. 7. The surgeon can then release the tension in the steering tether 160 to allow the snare loop 150 to resume its shape and encircle the polyp 18 as shown in FIG. 8. The snare loop 150 can then be cinched around the polyp 18 by moving the control slide 122 proximally relative to the body 112 of the snare control module 110. The snare loop 150 could be removed from the polyp 18 by reversing the above procedure.

This procedure and the steering tether 160 provide an extra degree of maneuverability of the snare. However, when the tube 132 is extended a long distance from the distal end of the cannula 50 or when the tube 132 has been passed through a series of bends in the cavity 14, it may be difficult to establish the necessary tension on the steering tether 160 or to assure that the tensile force is aligned in the desired direction.

Figure 9:
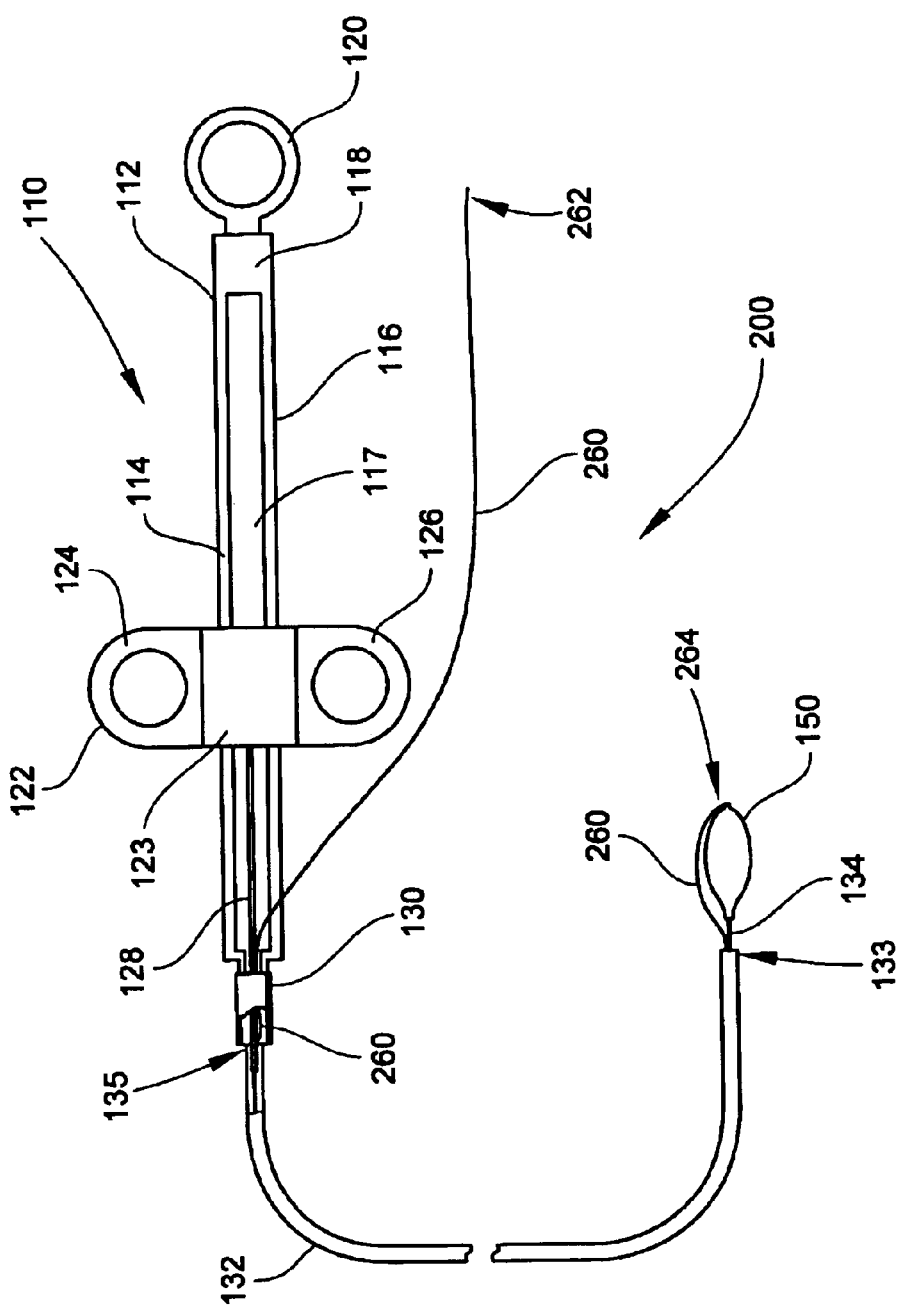
FIG. 9 is a partially sectioned view of a surgical instrument according to an embodiment of the invention.
Figure 10:
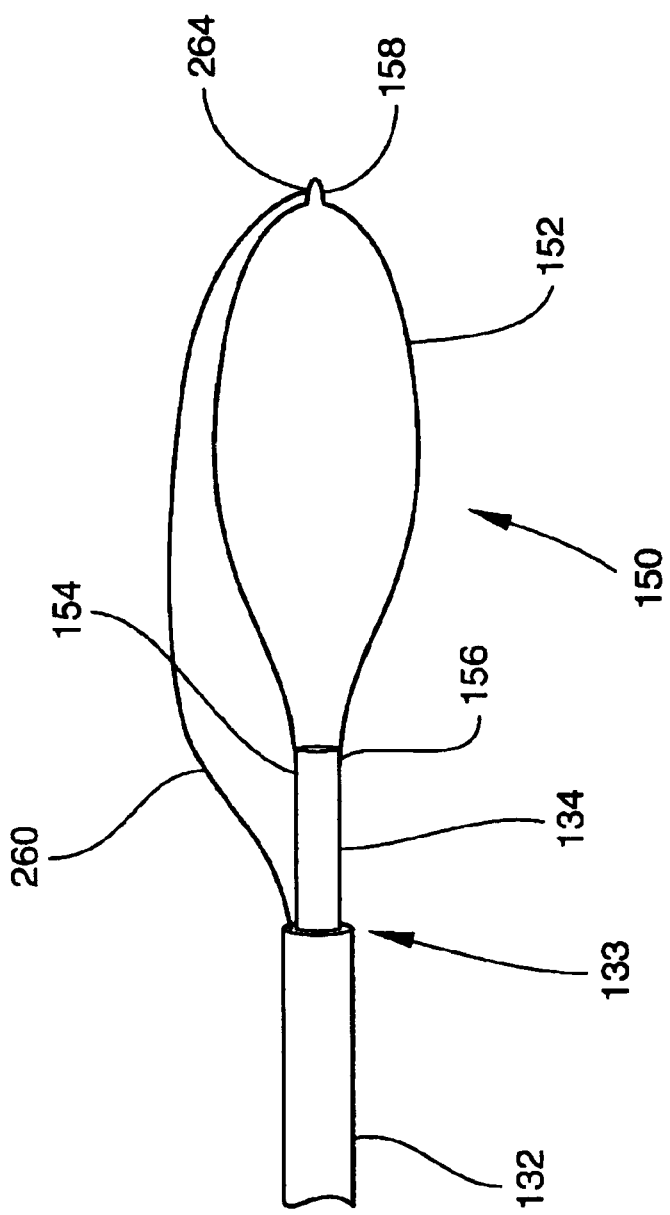
FIG. 10 is a perspective view of a snare loop of the surgical instrument illustrated in FIG. 9.

The present invention therefore provides an alternative configuration as illustrated by the surgical instrument 200 shown in FIGS. 9 and 10. The snare control module 110 and the snare loop 150 are substantially unchanged in this configuration. The surgical instrument 200, however, includes a steering tether 260 that is slidably disposed through the flexible tube 132 along with the cable 134. The tube 132 and, in particular, the interior diameter of the passage through the tube 132 may be sized so that the cable 134 and the steering tether 260 can be moved substantially independently within the tube 132. As shown in FIG. 10, the steering tether 260 passes out of the distal end 133 of the tube 132 along side the cable 134. In a manner similar to that described above, the distal end 264 of the steering tether 260 is attached to the loop member 152 so that tension applied to the steering tether 260 will cause the loop member 152 to be deformed.

As shown in FIG. 9, the steering tether 260 passes through the proximal end 135 of the tube 132 and through the connector 130 into the opening 117 between the frame members 114, 116. The proximal end 262 of the steering tether 260 can be thus be extended out from the body 112 of the snare control module 110 and may be secured in any of the above-described ways or may be left as a free end for a surgeon to tie off.

Figure 11:
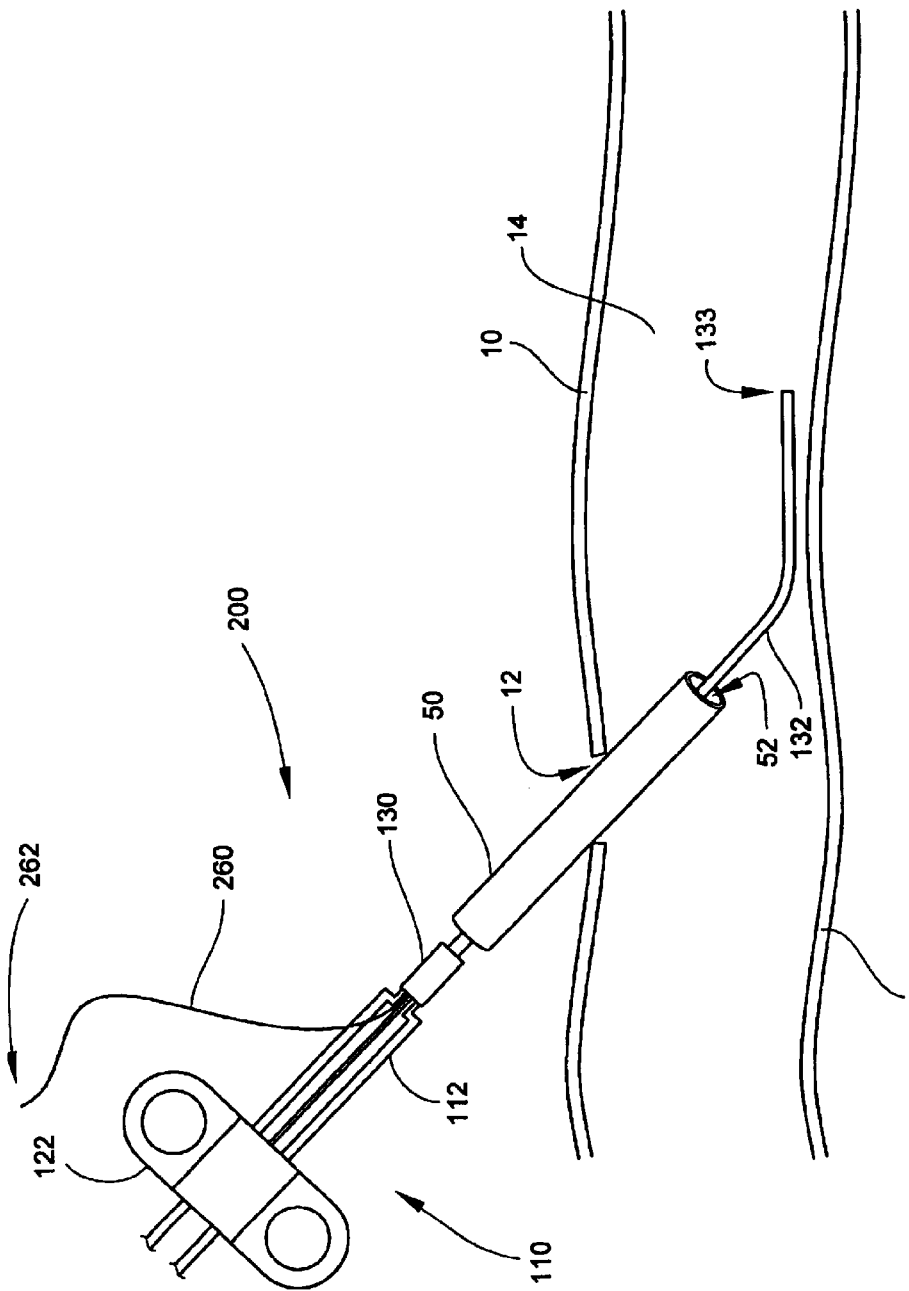
FIG. 11 is a view of the surgical instrument of FIG. 9 partially inserted into a body cavity through a cannula.
Figure 12:
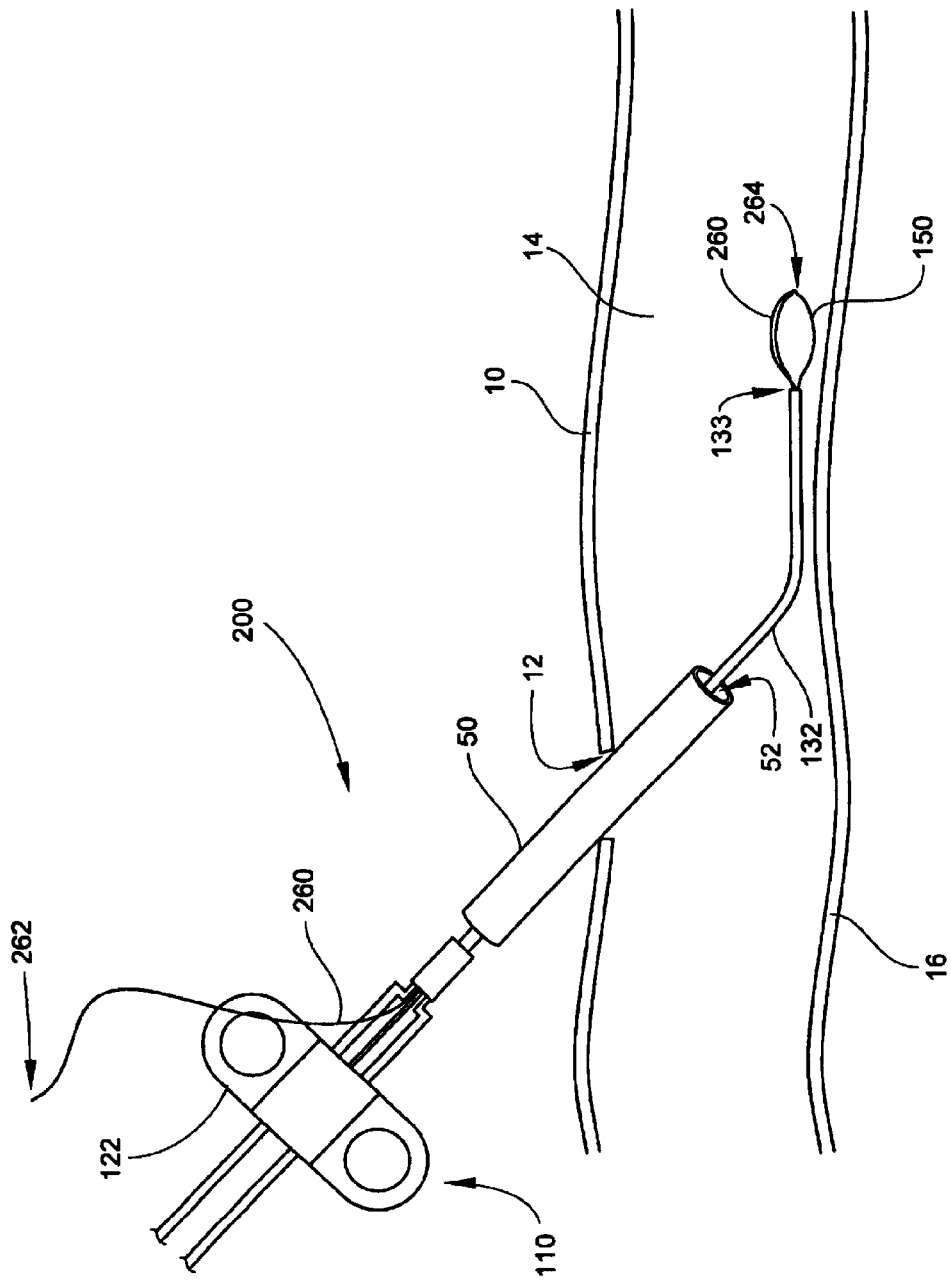
FIG. 12 is a view of the surgical instrument of FIG. 11 with its snare loop deployed.

Turning now to FIGS. 11 and 12, the flexible tube 132 and the snare loop 150 of the surgical instrument 200 may be introduced into a body cavity 14 through the lumen 52 of a cannula 50. The body cavity 14 is again defined by first and second tissue walls 10 and 16 and the cannula 50 is disposed through an opening 12 in the first tissue layer 10. The distal end 133 of the flexible tube 132 may be passed through the cannula 50 into the cavity 14 with the snare loop 150 retracted within the tube 132 as shown in FIG. 11. In this configuration, the distal end 264 of the steering tether 260, which is attached to the snare loop 150 is also withdrawn within the tube 132 so that none of the steering tether 260 extends out from the distal end 133 of the tube 132. The tube 132 can thus be easily inserted through the lumen 52 of the cannula 50 into the cavity 14.

Once the tube 132 has been inserted and positioned near the area of interest, the control slide 122 of the snare control module 110 can be moved in the distal direction relative to the body 112 to cause the snare loop 150 to be extended as shown in FIG. 12. It will be understood that, depending on the relative sizes of the snare loop 150 and the cannula lumen 52, it may be possible to insert the tube 132 through the cannula 50 with the snare loop 150 already deployed. In either case, the snare loop 150 and the steering tether 260 may be positioned within the cavity 14 as shown in FIG. 12.

Figure 13:
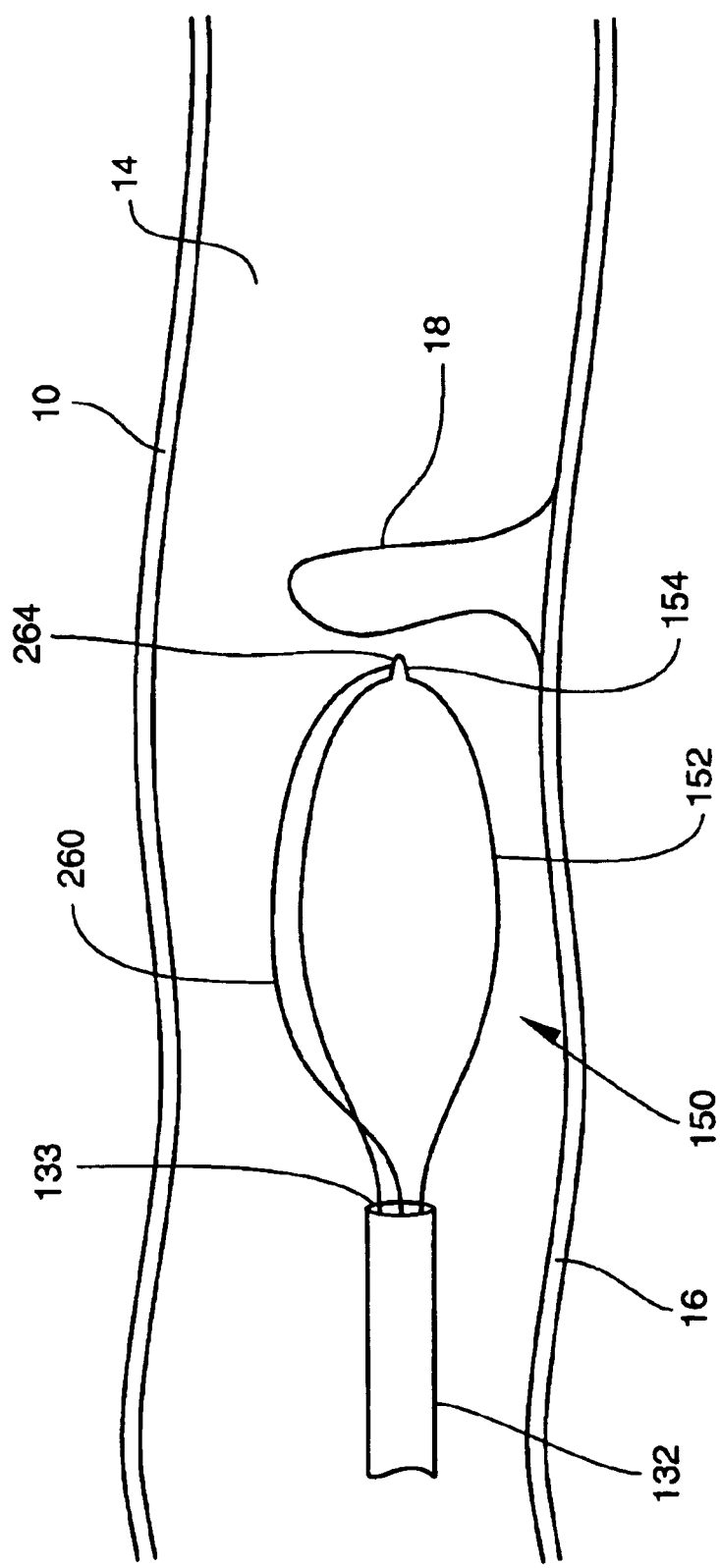
FIG. 13 is a perspective view of a snare loop of a surgical instrument according to the invention illustrating a step in a sequence of encircling a polyp with the snare loop.
Figure 14:
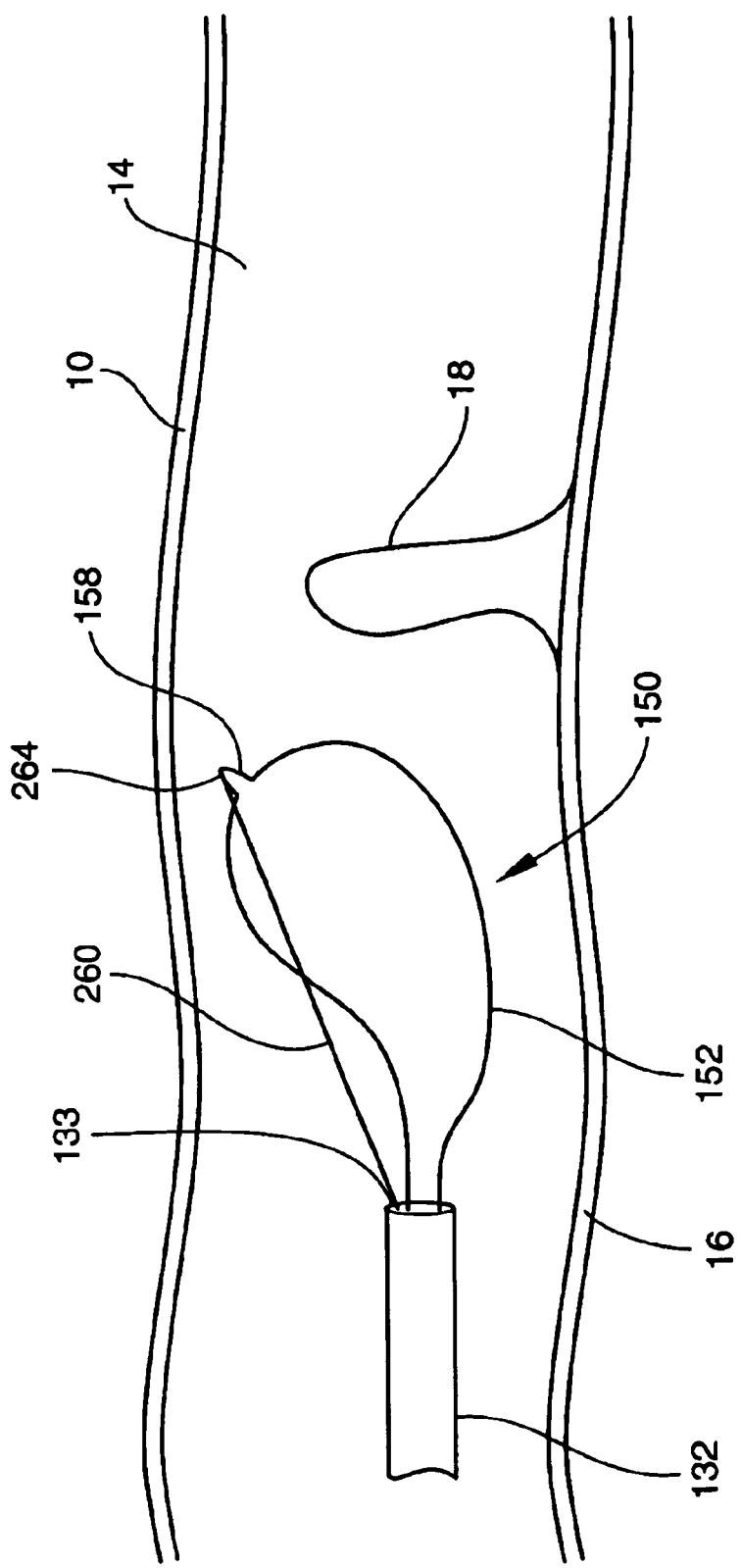
FIG. 14 is a perspective view of a snare loop of a surgical instrument according to the invention illustrating another step in a sequence of encircling a polyp with the snare loop.
Figure 15:
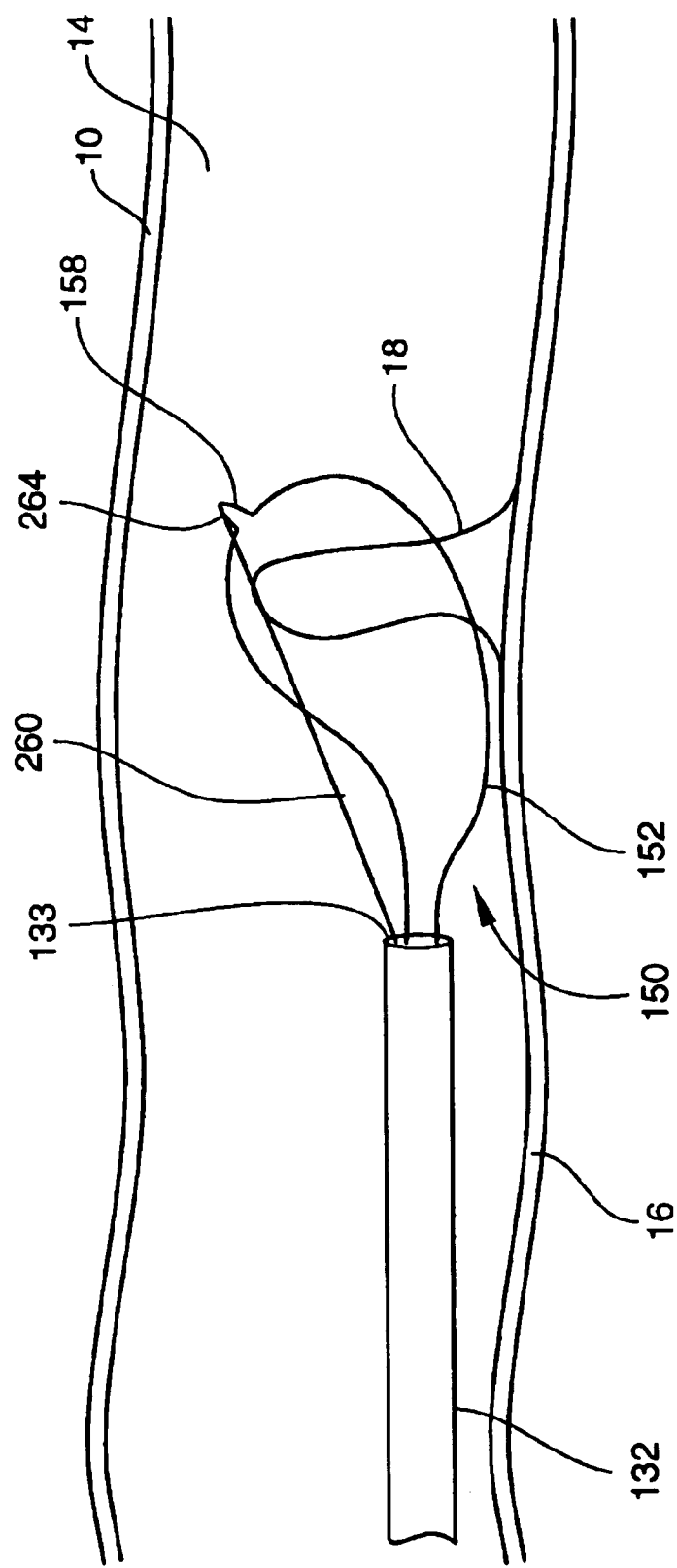
FIG. 15 is a perspective view of a snare loop of a surgical instrument according to the invention illustrating another step in a sequence of encircling a polyp with the snare loop.
Figure 16:
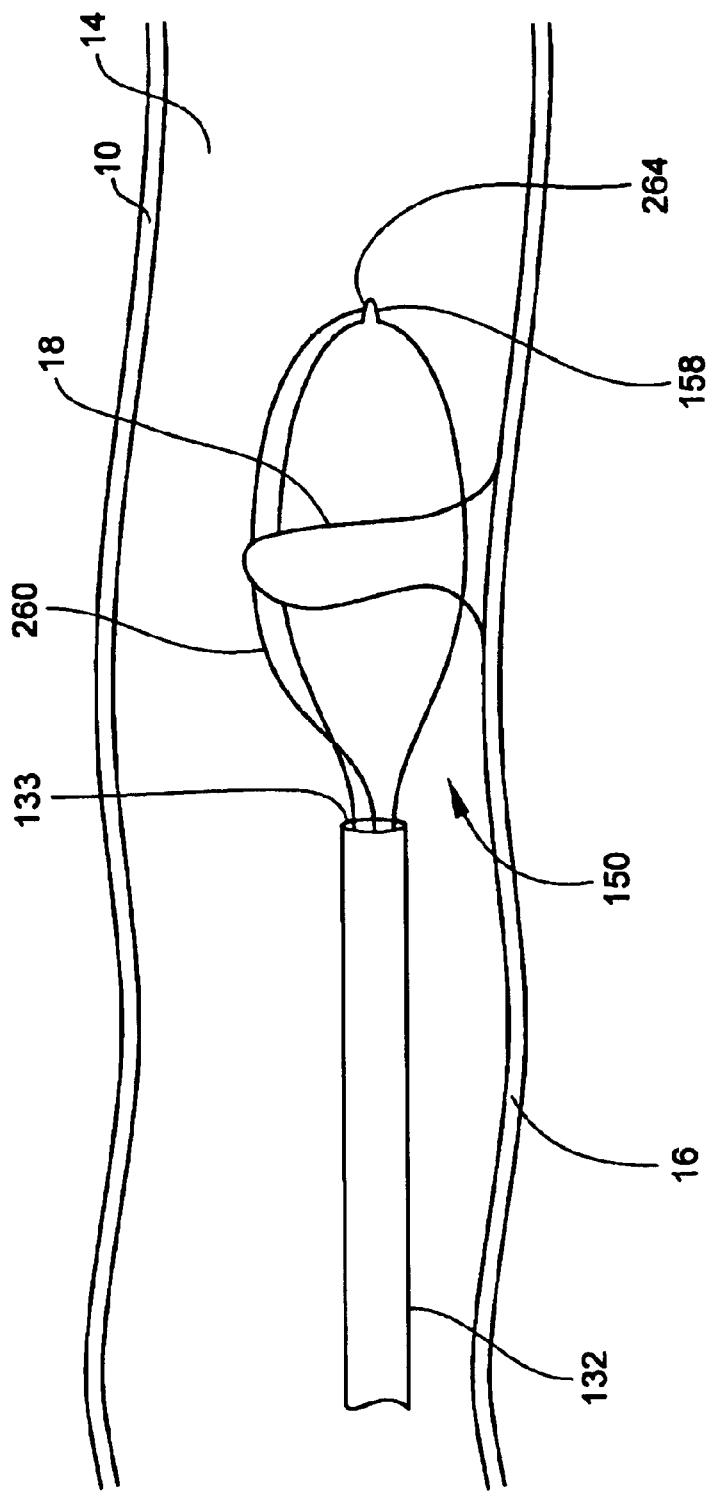
FIG. 16 is a perspective view of a snare loop of a surgical instrument according to the invention illustrating another step in a sequence of encircling a polyp with the snare loop.

FIGS. 13–16 illustrate a sequence by which the snare loop 150 of the surgical instrument 200 can be used to encircle a polyp 18 attached to the lower tissue wall 16. As initially deployed from the tube 132, the steering tether 260 is relatively slack and the snare loop 150 is at a level where it cannot be positioned over the top of the polyp 18 (FIG. 13). By pulling on the proximal end 262 of the steering tether 260, a surgeon can place the steering tether 260 in tension. As shown in FIG. 14, the tensile force transmitted through the steering tether 260 causes the snare loop 150 to be deformed so that the distal portion of the snare loop member 152 may be raised above the level of the polyp as shown in FIG. 14. Because the steering tether 260 is threaded through the flexible tube 132, the problems associated with the distance from the cannula 50 and possible bends in the cavity 14 are significantly reduced or eliminated. With the snare loop 150 raised, the tube 132 can then be translated further into the cavity 14 to position the snare loop 150 over the polyp 18 as shown in FIG. 15. The surgeon can then release the tension in the steering tether 260 to allow the snare loop 150 to resume its shape and encircle the polyp 18 as shown in FIG. 16. The snare loop 150 can then be cinched around the polyp 18 by moving the control slide 122 proximally relative to the body 112 of the snare control module 110. The snare loop 150 could be removed from the polyp 18 by reversing the above procedure.

As previously noted, the tethers 160, 260 of the surgical instruments 100, 200 of the present invention may be attached anywhere around the circumference of the loop member 152 of the snare loop 150. Accordingly, a steering tether 160, 260 could be attached to one side of the loop formed by the loop member 152. Tension applied to such a tether could be used to deform the snare loop 150 so as to steer it to the side. This allows the use of multiple tethers, each attached to a different circumferential point around the loop member 152 to allow steering of the snare loop 152 in a different direction.

Figure 17:
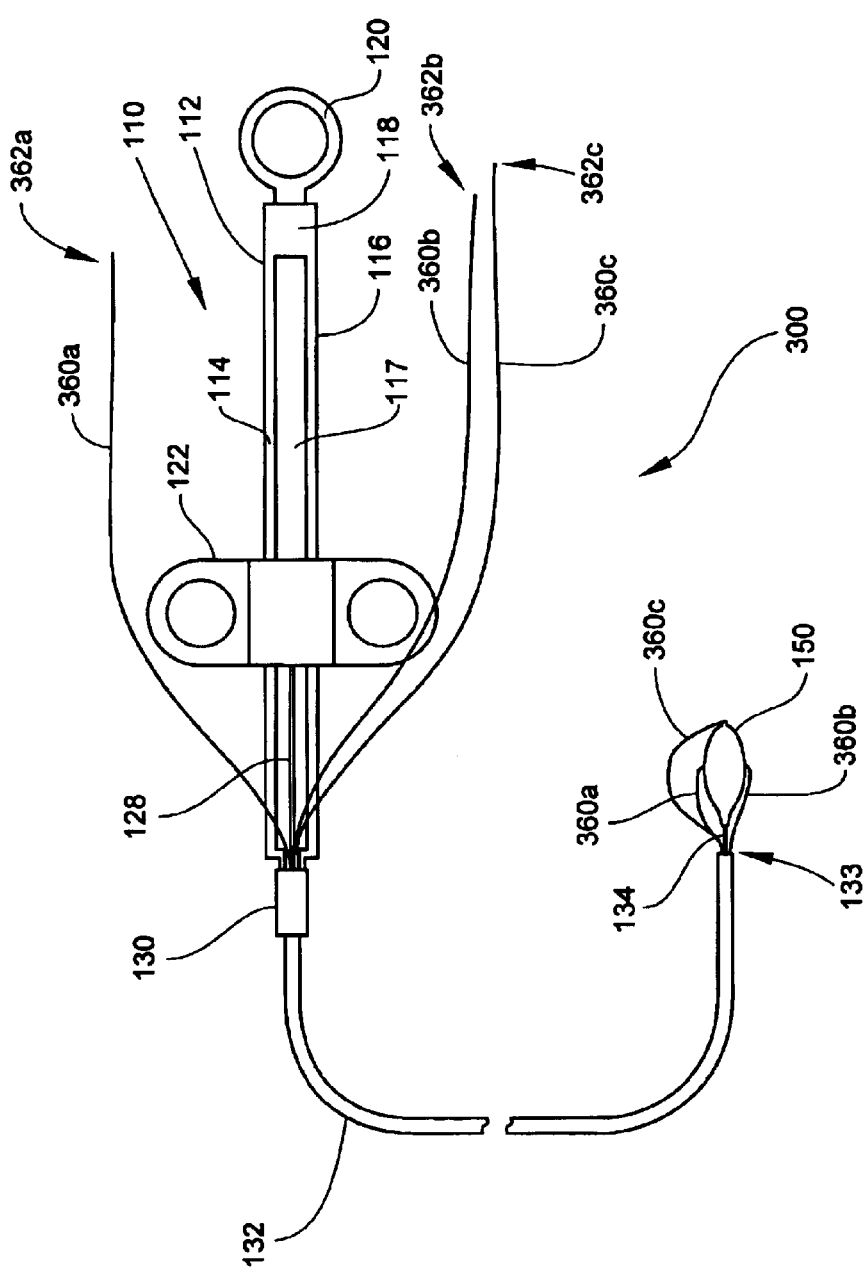
FIG. 17 is a partially sectioned view of a surgical instrument according to an embodiment of the invention.
Figure 18:
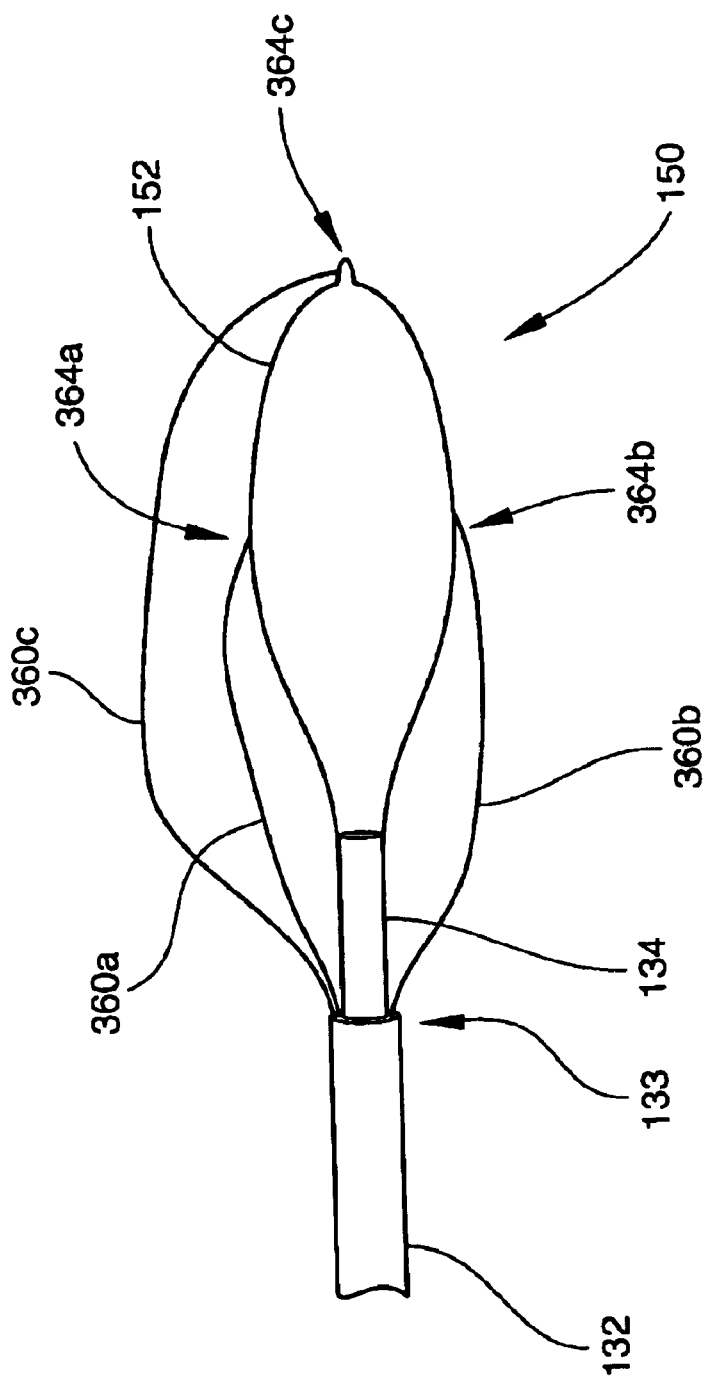
FIG. 18 is a perspective view of a snare loop of the surgical instrument illustrated in FIG. 17.

An exemplary surgical instrument 300 having multiple steering tethers 360a, 360b, 360c is illustrated in FIGS. 17 and 18. The snare control module 110 and the snare loop 150 are again substantially similar to those of the previous embodiments. The steering tethers 360a, 360b, 360c are slidably disposed through the flexible tube 132 along with the cable 134. The tube 132 and, in particular, the interior diameter of the passage through the tube 132 may be sized so that the cable 134 and the steering tethers 360a, 360b, 360c can be moved substantially independently within the tube 132. As shown in FIG. 10, the steering tethers 360a, 360b, 360c pass out of the distal end 133 of the tube 132 along side the cable 134. The distal end 364a of a first tether 360a is attached to one side of the snare loop 150. The distal end 364b of a second tether 360b is attached to the opposite side of the snare loop 150. The distal end 364c of a third tether 360c is attached to the distal tip of the snare loop 150.

As shown in FIG. 17, the steering tethers 360a, 360b, 360c pass through the tube 132 and through the connector 130 into the opening 117 between the frame members 114, 116. The proximal ends 362a, 362b, 362c of the steering tethers 360a, 360b, 360c can be thus be extended out from the body 112 of the snare control module 110 and may be secured in any of the above-described ways or may be left as free ends for a surgeon to tie off as desired.

The steering tethers 360a, 360b, 360c of the surgical instrument 300 are used in a manner similar to the tethers 160, 260 of the previous embodiments. The first and second steering tethers 360a, 360b may be used to steer the snare loop 150 from side to side and the third tether 360c may be used to raise the distal portion of the snare loop 150 as previously described. The steering tethers 360a, 360b, 360c may be used individually or in combination to maneuver the snare loop 150 as desired.

It will be understood that multiple steering tethers may also be used in an instrument configuration wherein the steering tethers are not disposed through the tube 132 but are instead separately passed out of the body cavity through the cannula in a manner similar to that described for the single steering tether 160 of the surgical instrument 100.

It will be understood that the steering tethers of the present invention may be applied to other forms of surgical snare. This includes snares with loops formed by a belt or wire having either or both ends passing out through a cannula. Such snares are typically cinched by applying tension to the free end (or ends) of the belt or wire. The steering tethers of the present invention could easily be attached to the loops of such snares.

Other embodiments and uses of the invention will be apparent to those skilled in the art from consideration of the specification and practice of the invention disclosed herein. The specification and examples should be considered exemplary only. The scope of the invention is limited only by the claims appended hereto.

What is claimed is:

1. A surgical instrument for facilitating the capture of objects during surgery, the instrument comprising:
    a flexible tube having a proximal tube end and a distal tube end, the flexible tube defining a cable passageway and being configured for insertion of at least a distal portion of the flexible tube into a body cavity of a patient;
    a flexible cable having a proximal cable end and a distal cable end, at least a portion of the flexible cable being slidably disposed in the cable passageway;

a snare loop having a loop member attached to the distal cable end, the snare loop and the cable being adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway, the loop member being adapted for selectively encircling and engaging at least a portion of an object in the body cavity; and a steering tether having a proximal tether end and a distal tether end, the distal tether end being fixedly attached to the loop member so that application of a tensile force to the proximal tether end causes the snare loop to deform in a predetermined manner, thereby facilitating a maneuvering of the snare loop.

2. A surgical instrument according to claim 1 further comprising means for selectively controlling the extension of the snare loop from and the retraction of the snare loop into the flexible tube.

3. A surgical instrument according to claim 1 further comprising a snare control module having a body with a distal body end to which the flexible tube is connected and a proximal body end, and a control slide with a passage formed therein for slidable disposition of at least a portion of the body therethrough, the control slide being connected to the proximal end of the flexible cable by a control rod so that movement of the control slide toward the proximal body end causes proximal movement of the flexible cable within the cable passageway and movement of the control slide toward the distal body end causes distal movement of the flexible cable within the cable passageway.

4. A surgical instrument according to claim 1 wherein the flexible tube is configured so that the at least a distal portion of the flexible tube can be inserted into a body cavity through a cannula with the snare loop disposed adjacent the distal tube end and wherein the steering tether is configured so that when the at least a portion of the flexible tube is inserted into the body cavity through the cannula, the proximal tether end can be selectively retained outside the body cavity.

5. A surgical instrument according to claim 4 wherein the steering tether is adapted to be extendible from the loop member through the cannula external to the flexible tube when the at least a distal portion of the flexible tube is inserted into a body cavity through the cannula.

6. A surgical instrument according to claim 1 further comprising means for securing the proximal tether end external to the body cavity.

7. A surgical instrument according to claim 1 wherein at least a first portion of the steering tether is slidably disposed within the cable passageway of the flexible tube and at least a second portion of the steering tether extends through the proximal end of the flexible tube.

8. A surgical instrument according to claim 1 wherein the surgical instrument comprises a plurality of steering tethers, each having a proximal tether end and a distal tether end attached to the loop member, each distal tether end being attached to a loop member portion so that application of a tensile force to the associated proximal tether end can be used to cause the loop member to deform in a different predetermined manner to facilitate maneuvering of the snare loop in an different predetermined direction.

9. A surgical instrument according to claim 1 wherein the snare loop includes an electrically conductive cauterization wire.

10. A surgical instrument for facilitating the capture of objects during surgery, the instrument comprising:

a snare control module having a body with a distal body end and a proximal body end, and a control slide with a passage formed therein for slidable disposition of at least a portion of the body therethrough;

a flexible tube having a proximal tube end attached to the distal end of the body and a distal tube end, the flexible tube defining a cable passageway and being configured for insertion of at least a distal portion of the flexible tube into a body cavity of a patient;

a flexible cable having a proximal cable end and a distal cable end, at least a portion of the flexible cable being slidably disposed in the cable passageway and the proximal cable end being connected to the control slide so that movement of the control slide toward the proximal body end causes proximal movement of the flexible cable within the cable passageway and movement of the control slide toward the distal body end causes distal movement of the flexible cable within the cable passageway;

a snare loop having a loop member attached to the distal cable end, the snare loop and the cable being adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway, the loop member being adapted for selectively encircling and engaging at least a portion of an object in the body cavity; and at least one steering tether having a proximal tether end and a distal tether end, the distal tether end being fixedly attached to the loop member so that application of a tensile force to the proximal tether end causes the snare loop to deform in a predetermined manner, thereby facilitating a maneuvering of the snare loop.

11. A surgical instrument according to claim 10 wherein the flexible tube is configured so that the at least a distal portion of the flexible tube can be inserted into a body cavity through a cannula with the snare loop disposed adjacent the distal tube end and wherein the at least one steering tether is configured so that when the at least a portion of the flexible tube is inserted into the body cavity through the cannula, the proximal tether end of the at least one steering tether can be selectively retained outside the body cavity.

12. A surgical instrument according to claim 11 further comprising means for securing at least one of the proximal tether end of the at least one steering tether external to the body cavity.

13. A surgical instrument according to claim 11 wherein the steering tether is adapted to be extendible from the loop member through the cannula external to the flexible tube when the at least a distal portion of the flexible tube is inserted into a body cavity through the cannula.

14. A surgical instrument according to claim 10 wherein at least a first portion of each of the at least one steering tether is slidably disposed within the cable passageway of the flexible tube and at least a second portion of each of the at least one steering tether extends through the proximal end of the flexible tube.

15. A surgical instrument according to claim 10 wherein the snare loop includes an electrically conductive cauterization wire.

16. A method of securing an object disposed within a body cavity of a patient using a surgical instrument having a flexible tube having distal and proximal tube ends and defining a cable passageway, a flexible cable having proximal and distal cable ends and being slidably disposed in the cable passageway, a snare loop attached to the distal cable end, the snare loop and the cable being adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway, and a steering tether having a proximal tether end and a distal tether end, the distal tether end being attached to the snare loop, the method comprising:

inserting the distal end of the flexible tube and the snare loop into the body cavity through a cannula while retaining the proximal tether end outside the body cavity;

maneuvering the distal end of the flexible tube through the body cavity until the snare loop is positioned adjacent the object;

placing the steering tether in tension by pulling on the proximal tether end;

applying a tensile force to the steering tether sufficient to cause the snare loop to deform in an efficacious manner to facilitate positioning of the snare loop around at least a portion of the object; and maneuvering the snare loop to encircle at least a portion of the object.

17. A method according to claim 16 wherein the step of maneuvering the snare loop to encircle at least a portion of the object includes releasing the tensile force on the steering tether to allow the snare loop to return to its predeformation shape.

18. A method according to claim 16 further comprising: cinching the snare loop to engage and secure the object.

19. A method according to claim 18 wherein the step of cinching the snare loop includes sliding the cable in a proximal direction within the cable passageway to retract at least a portion of the snare loop into the cable passageway.

20. A method according to claim 16 wherein the snare loop is initially disposed within the cable passageway of the flexible tube and the method further comprises:

sliding the cable in a distal direction within the cable passageway to extend at least a portion of the snare loop distally outward from the distal tube end.

21. A surgical instrument for facilitating the capture of objects during surgery, the instrument comprising:

a flexible tube having a proximal tube end and a distal tube end, the flexible tube defining a cable passageway and being configured for insertion of at least a distal portion of the flexible tube into a body cavity of a patient;

a flexible cable having a proximal cable end and a distal cable end, at least a portion of the flexible cable being slidably disposed in the cable passageway;

a snare loop having a loop member attached to the distal cable end, the snare loop and the cable being adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway, the loop member being adapted for selectively encircling and engaging at least a portion of an object in the body cavity; and a steering tether having a proximal tether end and a distal tether end, the distal tether end being attached to the loop member so that application of a tensile force to the proximal tether end causes the snare loop to deform in a predetermined manner, thereby facilitating a maneuvering of the snare loop, wherein the flexible tube is configured so that the at least a distal portion of the flexible tube can be inserted into a body cavity through a cannula with the snare loop disposed adjacent the distal tube end and wherein the steering tether is configured so that when the at least a portion of the flexible tube is inserted into the body cavity through the cannula, the proximal tether end can be selectively retained outside the body cavity, the steering tether being adapted to be extendible from the loop member through the cannula external to the flexible tube when the at least a distal portion of the flexible tube is inserted into a body cavity through the cannula.

22. A surgical instrument for facilitating the capture of objects during surgery, the instrument comprising:

a snare control module having a body with a distal body end and a proximal body end, and a control slide with a passage formed therein for slidable disposition of at least a portion of the body therethrough;

a flexible tube having a proximal tube end attached to the distal end of the body and a distal tube end, the flexible tube defining a cable passageway and being configured for insertion of at least a distal portion of the flexible tube into a body cavity of a patient;

a flexible cable having a proximal cable end and a distal cable end, at least a portion of the flexible cable being slidably disposed in the cable passageway and the proximal cable end being connected to the control slide so that movement of the control slide toward the proximal body end causes proximal movement of the flexible cable within the cable passageway and movement of the control slide toward the distal body end causes distal movement of the flexible cable within the cable passageway;

a snare loop having a loop member attached to the distal cable end, the snare loop and the cable being adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway, the loop member being adapted for selectively encircling and engaging at least a portion of an object in the body cavity; and at least one steering tether having a proximal tether end and a distal tether end, the distal tether end being attached to the loop member so that application of a tensile force to the proximal tether end causes the snare loop to deform in a predetermined manner, thereby facilitating a maneuvering of the snare loop, wherein the flexible tube is configured so that the at least a distal portion of the flexible tube can be inserted into a body cavity through a cannula with the snare loop disposed adjacent the distal tube end and wherein the at least one steering tether is configured so that when the at least a portion of the flexible tube is inserted into the body cavity through the cannula, the proximal tether end of the at least one steering tether can be selectively retained outside the body cavity, the steering tether being adapted to be extendible from the loop member through the cannula external to the flexible tube when the at least a distal portion of the flexible tube is inserted into a body cavity through the cannula.

23. A method of securing an object disposed within a body cavity of a patient using a surgical instrument having a flexible tube having distal and proximal tube ends and defining a cable passageway, a flexible cable having proximal and distal cable ends and being slidably disposed in the cable passageway, a snare loop attached to the distal cable end, the snare loop and the cable being adapted so that the snare loop can be selectively retracted within the cable passageway by sliding the flexible cable proximally within the cable passageway and so that at least a portion of the snare loop can be selectively extended from the distal tube end by sliding the flexible cable distally within the cable passageway, and a steering tether having a proximal tether end and a distal tether end, the distal tether end being attached to the snare loop, the method comprising:

inserting the distal end of the flexible tube and the snare loop into the body cavity through a cannula while retaining the proximal tether end outside the body cavity;

maneuvering the distal end of the flexible tube through the body cavity until the snare loop is positioned adjacent the object;

placing the steering tether in tension by pulling on the proximal tether end;

applying a tensile force to the steering tether sufficient to cause the snare loop to deform in an efficacious manner to facilitate positioning of the snare loop around at least a portion of the object; and releasing the tensile force on the steering tether to allow the snare loop to return to its predeformation shape to encircle at least a portion of the object.

24. A method according to claim 23 further comprising:

cinching the snare loop to engage and secure the object.

25. A method according to claim 24 wherein the step of cinching the snare loop includes sliding the cable in a proximal direction within the cable passageway to retract at least a portion of the snare loop into the cable passageway.

26. A method according to claim 23 wherein the snare loop is initially disposed within the cable passageway of the flexible tube and the method further comprises:

sliding the cable in a distal direction within the cable passageway to extend at least a portion of the snare loop distally outward from the distal tube end.

* * * * *